United States Patent [19]

Drabek

[11] Patent Number: 4,532,256
[45] Date of Patent: Jul. 30, 1985

[54] PESTICIDAL N-METHYL-CARBAMIC ACID ESTERS

[75] Inventor: Jozef Drabek, Oberwil, Switzerland

[73] Assignee: Ciba-Geigy Corporation, Ardsley, N.Y.

[21] Appl. No.: 560,655

[22] Filed: Dec. 12, 1983

[30] Foreign Application Priority Data

Dec. 24, 1982 [CH] Switzerland ............... 7534/82

[51] Int. Cl.³ ............... A01N 47/10; A01N 37/00; A01N 43/08; C07C 125/06
[52] U.S. Cl. ............... 514/469; 514/490; 514/477; 549/467; 549/470; 260/453.3; 560/134; 560/132; 560/160; 560/167; 560/29; 560/27
[58] Field of Search ............... 549/467, 470; 260/453.3; 560/134, 132, 160, 167, 29, 27; 424/300, 298, 285

[56] References Cited

U.S. PATENT DOCUMENTS 3,404,208 10/1968 Robertson et al. ............... 424/300
4,323,578 4/1982 Middleton ............... 260/453.3

FOREIGN PATENT DOCUMENTS 1693155 10/1971 Fed. Rep. of Germany ...... 424/300

*Primary Examiner*—Henry R. Jiles
*Assistant Examiner*—Robert C. Whittenbaugh
*Attorney, Agent, or Firm*—Edward McC. Roberts; Frederick H. Rabin

[57] ABSTRACT

N-Methyl-carbamic acid esters of the formula

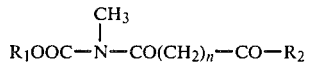

wherein
$R_1$ is unsubstituted or substituted 2,3-dihydrobenzofuranyl, phenyl, naphthyl or

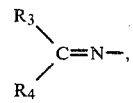

$R_2$ is hydroxyl, halogen, $-OR_1$, $C_1-C_{10}$-alkoxy, $C_2-C_{10}$-alkenyloxy, $C_1-C_{10}$-dialkylamino or

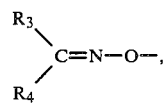

$R_3$ is hydrogen, $C_1-C_6$-alkyl or $C_2-C_3$-alkenyl,
$R_4$ is $C_1-C_6$-alkyl, $-SR_5$,

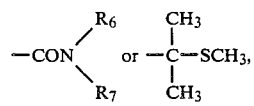

$R_5$ is $C_1-C_6$-alkyl or $C_2-C_3$-alkenyl,
$R_6$ and $R_7$ are each hydrogen or $C_1-C_6$-alkyl, and
n is zero or 1.

A process for producing these compounds and their use for combating pests are described.

13 Claims, No Drawings

PESTICIDAL N-METHYL-CARBAMIC ACID ESTERS

The present invention relates to N-methyl-carbamic acid esters, to processes for producing them, and to their use for controlling pests.

The N-methyl-carbamic acid esters have the formula (I)

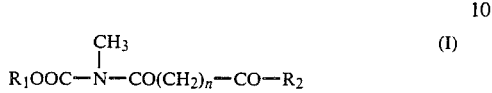

wherein
$R_1$ is unsubstituted or substituted 2,3-dihydrobenzofuranyl, phenyl or naphthyl or

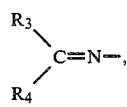

$R_2$ is hydroxyl, halogen, $-OR_1$, $C_1-C_{10}$-alkoxy, $C_2-C_{10}$-alkenyloxy, $C_1-C_{10}$-dialkylamino or

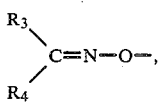

$R_3$ is hydrogen, $C_1-C_6$-alkyl or $C_2-C_3$-alkenyl,
$R_4$ is $C_1-C_6$-alkyl, $-SR_5$,

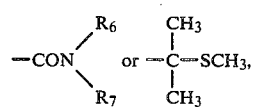

$R_5$ is $C_1-C_6$-alkyl or $C_2-C_3$-alkenyl,
$R_6$ and $R_7$ are each hydrogen or $C_1-C_6$-alkyl, and
n is zero or 1.

Substituents on the 2,3-dihydrobenzofuranyl, naphthyl or phenyl group can be halogen, $C_1-C_6$-alkoxy, $C_1-C_6$-alkylthio, amino, nitro, trifluoromethyl or $C_1-C_6$-alkyl, particularly methyl. By halogen in this case is meant fluorine, chlorine, bromine or iodine, especially chlorine.

The alkyl, alkoxy, alkylthio, alkenyl and alkenyloxy groups denoted by $R_2$ to $R_7$ can be straight-chain or branched-chain. The alkoxy and alkenyloxy groups for $R_2$ have in the chain preferably 1-6 and 2-3 carbon atoms, respectively.

Examples of alkyl, alkoxy, alkylthio, alkenyl and alkenyloxy groups denoted by $R_2$ and $R_3$ are: methyl, methoxy, methylthio, ethyl, ethoxy, $-CH_2-CH=CH_2$, $-O-CH_2-CH=CH_2$, propyl, propoxy, isopropyl, isopropoxy, n-butyl, n-butoxy, n-pentyl, n-pentoxy, n-hexyl, n-hexoxy and isomers thereof.

Preferred compounds of the formula I are those
wherein
$R_1$ is 2,3-dihydrobenzofuranyl or

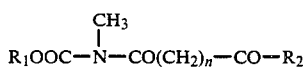

each unsubstituted or substituted by halogen, $C_1-C_6$-alkoxy, $C_1-C_6$-alkylthio, amino, nitro, trifluoromethyl or $C_1-C_6$-alkyl,
$R_2$ is chlorine, $-O-CH_2-CH=CH_2$, $-OR_1$, $C_1-C_6$-alkoxy, $-N(C_1-C_6$-alkyl$)_2$ or

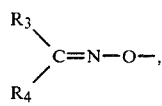

$R_3$ is hydrogen, $C_1-C_6$-alkyl or $-CH_2-CH=CH_2$,
$R_4$ is $C_1-C_6$-alkyl, $-SR_5$,

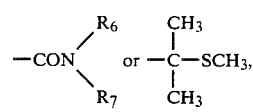

$R_5$ is $C_1-C_6$-alkyl or $-CH_2-CH=CH_2$,
$R_6$ and $R_7$ are each hydrogen or $C_1-C_6$-alkyl, and
n is zero or 1.

Compounds of the formula I particularly preferred are those
wherein
$R_1$ is 2,3-dihydrobenzofuranyl or

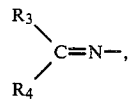

each unsubstituted or substituted by halogen, $C_1-C_6$-alkoxy, $C_1-C_6$-alkylthio, amino, nitro, trifluoromethyl or $C_1-C_6$-alkyl,
$R_2$ is chlorine, $-O-CH_2-CH=CH_2$, $-OR_1$, $C_1-C_6$-alkoxy, $-N(C_1-C_6$-alkyl$)_2$ or

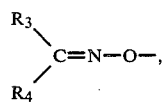

$R_3$ is hydrogen, $C_1-C_6$-alkyl or $-CH_2-CH=CH_2$,
$R_4$ is $C_1-C_6$-alkyl, $-SR_5$,

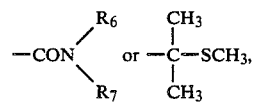

$R_5$ is $C_1-C_6$-alkyl or $-CH_2-CH=CH_2$,
$R_6$ and $R_7$ are each hydrogen or $C_1-C_6$-alkyl, and
n is 1;
or compounds of the formula I wherein
$R_1$ is 2,3-dihydrofuranyl or

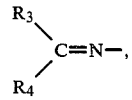

each unsubstituted or substituted by halogen, $C_1-C_6$-alkoxy, $C_1-C_6$-alkylthio, amino, nitro, trifluoromethyl or $C_1-C_6$-alkyl,
$R_2$ is

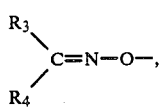

R₃ is hydrogen, $C_1-C_6$-alkyl or $-CH_2-CH=CH_2$,
R₄ is $C_1-C_6$-alkyl, $-SR_5$,

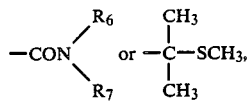

R₅ is $C_1-C_6$-alkyl or $-CH_2-CH=CH_2$,
R₆ and R₇ are each hydrogen or $C_1-CH_6$-alkyl, and
n is zero;
or compounds of the formula I wherein
R₁ is

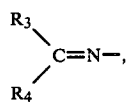

R₂ is chlorine, $-O-CH_2-CH=CH_2$, $-OR_1$, $C_1-C_6$-alkoxy or $-N(C_1-C_6$-alkyl)$_2$,
R₃ is hydrogen, $C_1-C_6$-alkyl or $-CH_2-CH=CH_2$,
R₄ is $C_1-C_6$-alkyl, $-SR_2$,

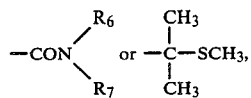

R₅ is $C_1-C_6$-alkyl or $-CH_2-CH=CH_2$,
R₆ and R₇ are each hydrogen or $C_1-C_6$-alkyl, and
n is zero.
More especially preferred are compounds of the formula I
wherein
R₁ is 2,3-dihydrobenzofuranyl which is unsubstituted or substituted by halogen, $C_1-C_6$-alkoxy, $C_1-C_6$-alkylthio, amino, nitro, trifluoromethyl or $C_1-C_6$-alkyl,
R₂ is

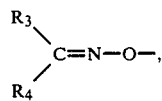

R₃ is hydrogen, $C_1-C_6$-alkyl or $-CH_2-CH=CH_2$,
R₄ is $C_1-C_6$-alkyl, $-SR_5$,

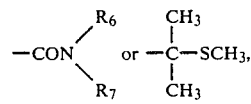

R₅ is $C_1-C_6$-alkyl or $-CH_2-CH=CH_2$,
R₆ and R₇ are each hydrogen or $C_1-CH_6$-alkyl, and
n is zero; or
R₁ is 2,3-dihydrobenzofuranyl which is unsubstituted or substituted by halogen, $C_1-C_6$-alkoxy, $C_1-C_6$-alkylthio, amino, nitro, trifluoromethyl or $C_1-C_6$-alkyl, R₂ is chlorine, $-O-CH_2-CH=CH_2$, $-OR_1$, $C_1-C_6$-alkoxy, $-N(C_1-CH_6$-alkyl)$_2$ or

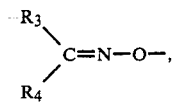

R₃ is hydrogen, $C_1-C_6$-alkyl or $-CH_2-CH=CH_2$,
R₄ is $C_1-C_6$-alkyl, $-SR_5$,

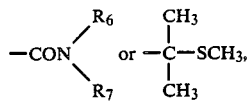

R₅ is $C_1-C_6$-alkyl or $-CH_2-CH=CH_2$,
R₆ and R₇ are each hydrogen or $C_1-CH_6$-alkyl, and
n is 1.

The compounds of the formula I can be produced by methods known per se, for example as follows:

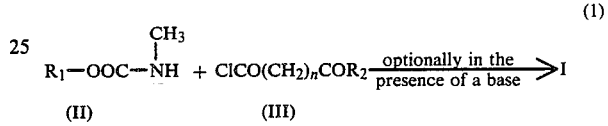

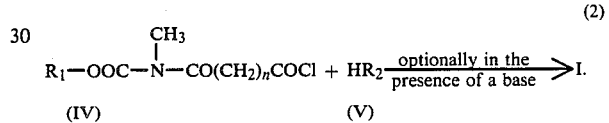

In the formulae II to V, the symbols R₁ and R₂ have the meanings defined under the formula I.

Suitable bases are in particular: tertiary amines, such as trialkylamines, dialkylamines, or p-dialkylaminopyridines; also hydroxides, oxides, carbonates and bicarbonates of alkali metals and alkaline-earth metals, as well as alkali metal alcoholates, for example potassium tert-butylate and sodium methylate.

The process is performed under normal pressure at a temperature of −25° to 150° C., preferably between −20° and 100° C., and optionally in a solvent or diluent. Suitable solvents or diluents are for example: ethers and ethereal compounds, such as diethyl ether, diisopropyl ether, dioxane and tetrahydrofuran; aliphatic and aromatic hydrocarbons, especially benzene, toluene and xylenes; and ketones, such as acetone, methyl ethyl ketone and cyclohexanone.

The starting materials of the formulae II to V are known, or they can be produced by methods analogous to known methods.

The compounds of the formula I are suitable for controlling pests on animals and plants and in the soil.

The compounds of the formula I are particularly suitable for controlling insects, for example of the orders: Lepidoptera, Coleoptera, Homoptera, Heteroptera, Diptera, Thysanoptera, Orthoptera, Anoplura, Siphonaptera, Mallophage, Thysanura, Isoptera, Psocoptera and Hymenoptera; and also phytopathogenic mites and ticks of the order Acarina. The compounds of the formula I exhibit also a good nematocidal action.

The compounds of the formula I are especially suitable for controlling insects that damage plants, in particular insects that damage plants by eating, in crops of ornamental plants and productive plants, particularly in cotton crops (for example against *Spodoptera littoralis* and *Heliothis virescens*); and also in vegetable crops (for example against *Leptinotarsa decemlineata* and *Myzus persicae*); and in rice crops (for example against *Chilo suppressalis* and *Nilaparvata lugens*) and for controlling soil insects (for example *Aulacophora femoralis, Chortophila brassicae, Pachmoda savignyi* and *Scotia ypsilon*).

It is to be emphasised in this connection that the said compounds are distinguished by both a strongly marked systemic action and contact action against sucking insects, especially against insects of the Aphididae family (for example *Aphis fabae, Aphis craccivora* and *Myzus persicae*), which are difficult to control with known compositions.

Active substances of the formula I exhibit a very good action also against flies, for example *Musca domestica*, and against mosquito larvae. Furthermore, they are distinguished by a broad ovicidal and ovilarvicidal action, and have a valuable action against ectoparasitic mites and ticks, for example of the families: Ixodidae, Argasidae and Dermanyssidae.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active ingredient of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid, or of a naphthalenesulfonic acid-formaldehyde condensation product. Also suitable are corresponding phosphates, for example salts of the phosphoric ester of a p-nonylphenol-(4–14)-ethylene oxide adduct, and phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenol-polyethoxyethanols, castor oil polyglycol ethers, polypropylene/polyethyleneoxy adducts, tributylphenoxy-polyethoxyethanol, polyethylene glycol and octylphenoxy-polyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publication:

"Mc Cutcheon's Detergents and Emulsifiers Annula", MC Publishing Corp., Ringwood, N.J., 1979;
Dr. Helmut Stache "Tensid Taschenbuch", Carl Hauser Verlag München/Wien 1981.

The pesticidal preparations contain as a rule 0.1 to 99%, particularly 0.1 to 95%, of active ingredient of the formula I, 1 to 99.9% of a solid or liquid additive, and 0 to 25%, especially 0.1 to 25% of a tenside.

Whereas commercial products are preferably in the form of concentrated compositions, the compositions employed by the end-user are as a rule diluted.

The compositions can also contain further additives such as stabilisers, antifoam agents, viscosity regulators, binders and adhesives, as well as fertilisers or other active ingredients for obtaining special effects.

Formulation examples for liquid active ingredients of the formula I (% = percent by weight)

| 1. Emulsion concentrates | a | b | c |
| --- | --- | --- | --- |
| active ingredient | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 2. Solutions | a | b | c | d |
| --- | --- | --- | --- | --- |
| active ingredient | 80% | 10% | 5% | 95% |
| ethylene glycol-monomethyl ether | 20% | — | — | — |
| polyethylene glycol M.W. 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

These solutions are suitable for application in the form of very small drops.

| 3. Granulates | a | b |
| --- | --- | --- |
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | a | b |
| --- | --- | --- |
| active ingredient | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

Formulation examples for solid active ingredients of the formula I (% = percent by weight)

| 5. Wettable powders | a | b | c |
| --- | --- | --- | --- |
| active ingredient | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of the required concentration are obtained.

| 6. Emulsion concentrate | |
| --- | --- |
| active ingredient | 10% |
| octylphenol polyethylene glycol ether (4–5 mols of ethylene oxide) | 3% |
| calcium dodecylbenzene sulfonate | 3% |
| castor oil polyglycol ether (36 mols of ethylene oxide) | 4% |
| cyclohexanone | 30% |
| xylene mixture | 50% |

Emulsions of the concentration required can be obtained from this concentrate by dilution with water.

| 7. Dusts | a | b |
| --- | --- | --- |
| active ingredient | 5% | 8% |
| talcum | 95% | — |
| kaolin | — | 92% |

Dusts ready for use are obtained by mixing the active ingredient with the carrier, and grinding the mixture in a suitable mill.

| 8. Extruder granulate | |
| --- | --- |
| active ingredient | 10% |
| sodium lignin sulfonate | 2% |
| carboxymethyl cellulose | 1% |
| kaolin | 87% |

The active ingredient is mixed and ground with the additives, and the mixture is moistened with water. This mixture is extruded and then dried in a stream of air.

| 9. Coated granulate | |
| --- | --- |
| active ingredient | 3% |
| polyethylene glycol (M.W. 200) | 3% |
| kaolin | 94% |

The finely ground active ingredient is evenly applied, in a mixer, to the kaolin moistened with polyethylene glycol. Dustfree coated granulates are obtained in this manner.

| 10. Suspension concentrate | |
| --- | --- |
| active ingredient | 40% |
| ethylene glycol | 10% |
| nonylphenolpolyethylene glycol ether (15 mols of ethylene oxide) | 6% |
| sodium lignin sulfonate | 10% |

-continued

| 10. Suspension concentrate | |
|---|---|
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is obtained a suspension concentrate from which can be produced, by dilution with water, suspensions of the concentration required.

EXAMPLE 1

(a) Production of N-chloroxalyl-N-methyl-7-(2,2-dimethyl-2,3-dihydrobenzofuranyl)-carbamate 25.38 g of oxalyl chloride are added dropwise to a suspension of 22.13 g of N-methyl-7-(2,2-dimethyl-2,3-dihydrobenzofuranyl)carbamate in 100 ml of 1,2-dichloroethane, and the reaction mixture is stirred at 65° C. for 4 hours. After cooling, the mixture is filtered, and the solvent is distilled off from the filtrate. The crude product remaining as residue after distillation is then recrystallised from hexane to thus obtain the compound No. 1 of the formula

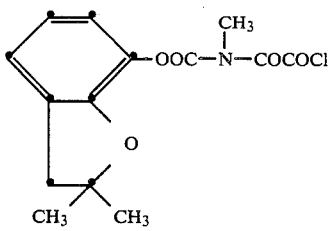

having a melting point of 99°–101° C.

(b) Production of N-ethoxycarbonyl-N-methyl-7-(2,2-dimethyl-2,3-dihydrobenzofuranyl)-carbamate To a solution of 9.35 g of N-chloroxalyl-N-methyl-7-(2,2-dimethyl-2,3-dihydrobenzofuranyl)-carbamate in 100 ml of toluene is added dropwise at 10° C., with stirring and cooling, a mixture of 1.52 g of ethanol and 4.56 ml of triethylamine. The mixture is stirred at 20° C. for 3 hours, and is then filtered with suction. After the toluene has been distilled off from the filtrate, the residue is recrystallised in a mixture of hexane/ether (1:1).

There is thus obtained the compound No. 2 of the formula

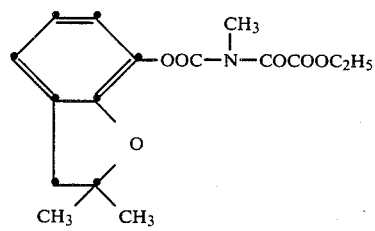

having a melting point of 82° C.

The following compounds are produced in an analogous manner:

$$R_1-OOC-\underset{\underset{CH_3}{|}}{N}-CO(CH_2)_nCO-R_2$$

| No. | $R_1$ | n | $R_2$ | Physical data |
|---|---|---|---|---|
| 3 | ![structure] | 0 | $-OCH_3$ | $n_D^{40°} = 1,5170$ |
| 4 | " | 0 | $-OC_3H_7(n)$ | m.p. 55–58° C. |
| 5 | " | 0 | $-OC_3H_7(i)$ | m.p. 60° C. |
| 6 | " | 0 | $-OC_4H_9(n)$ | $n_D^{40°} = 1,5018$ |
| 7 | " | 0 | $-OC_4H_9(i)$ | |
| 8 | " | 0 | $-OCH_2-CH=CH_2$ | $n_D^{40°} = 1,5135$ |
| 9 | " | 0 | $-O-\bigcirc$ | m.p. 127–128° C. |
| 10 | " | 0 | $-O-\bigcirc-CH_3$ | m.p. 120° C. |

-continued

| No. | R₁ | n | R₂ | Physical data |
|---|---|---|---|---|
| 11 | " | 0 | —O—⟨C₆H₄⟩—Cl | m.p. 140° C. |
| 12 | " | 0 | —N(C₂H₅)₂ | $n_D^{40°} = 1,5174$ |
| 13 | " | 0 | —N(C₃H₇n)₂ | $n_D^{40°} = 1,5104$ |
| 14 | " | 0 | —N(C₄H₉n)₂ | m.p. 47–52° |
| 15 | " | 0 | —ON=C(CH₃)₂ | resin |
| 16 | " | 0 | —ON=C(CH₃)(SCH₃) | m.p. 127–128° C. |

$$R_1OOC-N(CH_3)-CO(CH_2)_nCO-R_2$$

| No. | R₁ | n | R₂ | Physical data |
|---|---|---|---|---|
| 17 | 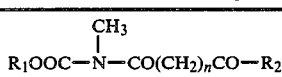 (2,6-dimethyl-4-neopentyloxyphenyl) | 0 | —ON=C(CH₃)(SC₂H₅) | m.p. 88–92° C. |
| 18 | " | 0 | —ON=C(SCH₃)(CON(CH₃)₂) | $n_D^{40°} = 1,5377$ |
| 19 | " | 0 | —ON=CH—C(CH₃)₂—SCH₃ | m.p. 90–95° C. |
| 20 | " | 0 | —O—⟨C₆H₃(CH₃)⟩—OC(CH₃)₂CH₂ | m.p. 133–135° C. |
| 21 | " | 1 | —OCH₃ | $n_D^{40°} = 1,5110$ |
| 22 | " | 1 | —OC₂H₅ | $n_D^{40°} = 1,5050$ |
| 23 | (4-isopropylphenyl) | 0 | —Cl | $n_D^{40°} = 1,5133$ |
| 24 | " | 0 | —OCH₃ | $n_D^{40°} = 1,5017$ |
| 25 | " | 0 | —O—⟨C₆H₅⟩ | $n_D^{40°} = 1,5370$ |

-continued

| No. | Structure | | | Properties |
|---|---|---|---|---|
| 26 | " | 0 | $-N(C_2H_5)_2$ | $n_D^{40°} = 1.5100$ |
| 27 | 4-(i)C$_3$H$_7$O-phenyl | 0 | $-O-$phenyl | $n_D^{40°} = 1.5287$ |
| 28 | $(CH_3S)(CH_3)C=N-$ | 0 | $-OC_2H_5$ | m.p. 91–92° C. |
| 29 | 2,5-dimethyl-4-(CH$_3$S)-phenyl | 0 | $-OC_2H_5$ | m.p. 68–70° C. |
| 30 | naphthyl | 0 | $-OC_2H_5$ | resin |
| 31 | 2-(neopentyl)-phenyl [CH$_2$-C(CH$_3$)$_3$ substituent via O] | 0 | $-N(CH_3)_2$ | $n_D^{40°} = 1.5211$ |
| 32 | " | 0 | $-N(C_3H_7(i))_2$ | m.p. 87–89° C. |

EXAMPLE 2

Insecticidal systemic action: Aphis craccivora

Rooted bean plants are transplanted to pots each containing 600 ccm of soil; and 50 ml of a test solution containing 25 ppm, 5 ppm and 1 ppm, respectively, of the compound to be tested are subsequently poured directly onto the soil. After 24 hours, aphids (Aphis craccivora) are settled onto the parts of plants above the soil, and a plastics cylinder is placed over each plant and drawn to by tying at the bottom in order to protect the aphids from any contact or gas effects of the test substance. An evaluation of the mortality rate achieved is made 48 hours after commencement of the test. Two plants, each in a separate pot, are used per concentration level of test substance. The test is carried out at 25° C. with 70% relative humidity.

The compounds according to Example 1 exhibit against Aphis craccivora the degree of activity shown in the following Table.

Biological test results

In the following Table are summarised test results based on the Example given in the foregoing, the index of values with regard to the percentage mortality of the pests being as follows:

A: 70–100% mortality with 1 ppm of active ingredient,
B: 70–100% mortality with 5 ppm of active ingredient,
C: 70–100% mortality with 25 ppm of active ingredient.

| Compound No. | Activity against Aphis craccivora |
|---|---|
| 1 | A |
| 2 | A |
| 3 | A |
| 4 | B |
| 5 | C |
| 6 | B |
| 7 | B |
| 8 | A |
| 9 | C |
| 10 | C |
| 11 | B |
| 12 | C |
| 13 | C |
| 14 | C |
| 15 | A |
| 16 | A |
| 17 | A |
| 18 | B |
| 19 | A |
| 20 | C |

| Compound No. | Activity against *Aphis craccivora* |
|---|---|
| 21 | B |
| 22 | B |
| 23 | B |
| 24 | B |
| 25 | B |
| 26 | C |
| 27 | B |
| 28 | A |
| 29 | B |
| 30 | A |
| 31 | A |

What is claimed is:

1. An N-methyl-carbamic acid ester of the formula

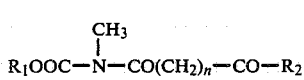

wherein
$R_1$ is

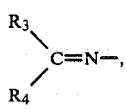

or is 2,3-dihydrobenzofuranyl, naphthyl or phenyl optionally substituted by halogen, $C_1-C_6$-alkoxy, $C_1-C_6$-alkylthio, amino, nitro, trifluoromethyl or $C_1-C_6$ alkyl, $R_2$ is hydroxyl, halogen, $-OR_1$, $C_1-C_{10}$-alkoxy, $C_2-C_{10}$-alkenyloxy, di-$(C_1-C_{10}$-alkyl)-amino or

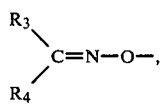

$R_3$ is hydrogen, $C_1-C_6$-alkyl or $C_2-C_3$-alkenyl,
$R_4$ is $C_1-C_6$alkyl, $-SR_5$

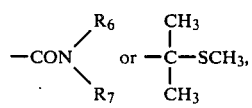

$R_5$ is $C_1-C_6$ alkyl or $C_2-C_3$-alkenyl,
$R_6$ and $R_7$ are each hydrogen or $C_1-C_6$-alkyl, and
n is zero or 1.

2. A compound according to claim 1 wherein $R_1$ is

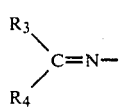

or optionally substituted 2,3-dihydrobenzofuranyl, $R_2$ is chlorine, $-OCH_2-CH=CH_2$, $OR_1$, $C_1-C_6$-alkoxy, $-N(C_1-C_6\text{-alkyl})_2$ or

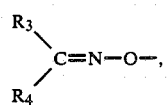

$R_3$ is hydrogen, $C_1-C_6$-alkyl or $-CH_2-CH=CH_2$, and
$R_5$ is $C_1-C_6$ alkyl or $-CH_2-CH=CH_2$.

3. The compound according to claim 2 of the formula

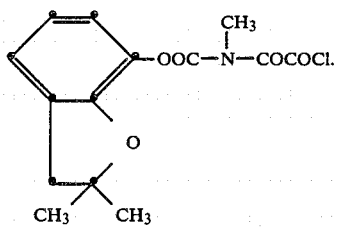

4. The compound according to claim 2 of the formula

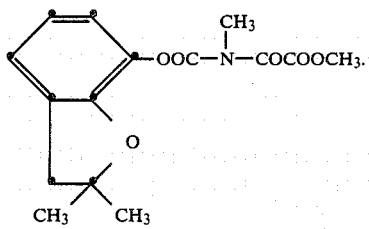

5. The compound according to claim 2 of the formula

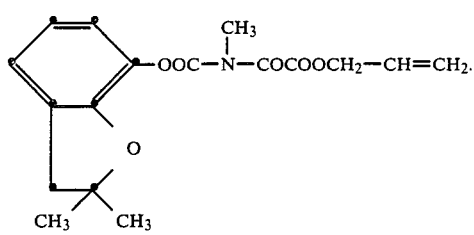

6. The compound according to claim 1 of the formula

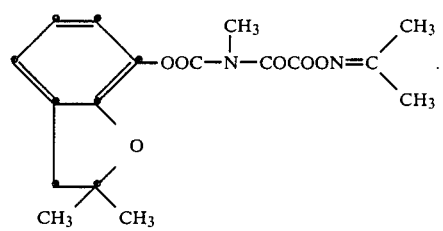

7. An insecticidal, acaricidal and nematocidal composition which contains as active ingredient a pesticidally effective amount of a compound according to claim 1, together with suitable solid or liquid additives.

8. A method of combating insects acarids and nematodes on animals and plants as well as in the soil, which method comprises applying thereto or to the locus thereof a pesticidally effective amount of a compound according to claim 1.

9. A compound according to claim 2 in which n is 1.

10. A compound according to claim 2 in which $R_2$ is

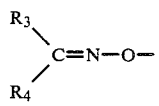

and n is zero.

11. A compound according to claim 2 wherein $R_1$ is

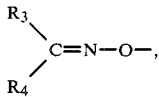

$R_1$ is chlorine, $-O-CH_2-CH=CH_2$, or $R_1$, $C_1$-$C_6$ alkoxy or $-N(C_1$-$C_6$-alkyl$)_2$, and n is zero.

12. A compound according to claim 2 wherein $R_1$ is optionally substituted 2,3-dihydrobenzofuranyl, $R_2$ is $$\begin{array}{c} R_3 \\ \diagdown \\ C=N-O-, \\ \diagup \\ R_4 \end{array}$$

n is zero.

13. A compound according to claim 2 in which $R_1$ is optionally substituted 2,3-dihydrobenzofuranyl and n is 1.

* * * * *